United States Patent [19]

Kline

[11] Patent Number: 5,127,268
[45] Date of Patent: * Jul. 7, 1992

[54] SYSTEM FOR NONDESTRUCTIVELY DETERMINING COMPOSITE MATERIAL PARAMETERS

[75] Inventor: Ronald A. Kline, Norman, Okla.

[73] Assignee: The Board of Regents for the University of Oklahoma, Norman, Okla.

[*] Notice: The portion of the term of this patent subsequent to Jul. 16, 2008 has been disclaimed.

[21] Appl. No.: 556,087

[22] Filed: Jul. 20, 1990

Related U.S. Application Data

[63] Continuation-in-part of Ser. No. 371,653, Jun. 21, 1989, Pat. No. 5,031,457, which is a continuation of Ser. No. 309,004, Feb. 7, 1989, abandoned, which is a continuation of Ser. No. 147,155, Jan. 22, 1988, abandoned.

[51] Int. Cl.⁵ .............................................. G01N 29/00
[52] U.S. Cl. ......................................... 73/597; 73/602
[58] Field of Search ................. 73/588, 598, 597, 602, 73/38

[56] References Cited

U.S. PATENT DOCUMENTS

| | | | |
|---|---|---|---|
| 3,720,098 | 3/1973 | Dixon | 73/597 |
| 3,995,501 | 12/1976 | Wiley | 73/597 |
| 4,745,809 | 5/1988 | Collins et al. | 73/597 |
| 5,031,457 | 7/1991 | Kline | 73/597 |

Primary Examiner—Hezron E. Williams
Assistant Examiner—Louis M. Arana
Attorney, Agent, or Firm—Ladas & Parry

[57] ABSTRACT

A method and apparatus for nondestructively determining fiber volume fraction and resin porosity of a composite material constructed of at least two different constituent materials wherein the following parameters of the composite material to be tested are known: density, elastic moduli of the constituent materials and layup sequence. Two acoustic waves of different polarizations are propagated through the composite material and the acoustic waves propagated through the composite material are sensed and the velocity of each of the two acoustic waves, $V_1$ and $V_2$, are determined. The thickness of the composite material is determined. The fiber volume fraction and resin porosity of the composite material are then determined using the velocities, $V_1$ and $V_2$, the thickness and known parameters of density, elastic moduli of the constituent materials and layup sequence.

14 Claims, 4 Drawing Sheets

SPECIMEN GEOMETRY

VS vs VL (UNDIRECTIONAL LAMINATE)

5,127,268

SYSTEM FOR NONDESTRUCTIVELY DETERMINING COMPOSITE MATERIAL PARAMETERS

CROSS REFERENCE TO RELATED APPLICATIONS

This application is a Continuation-in-Part of co-pending U.S. patent application Ser. No. 07/371,653, filed 21 Jun. 1989, now U.S. Pat. No. 5,031,457 which application is a Continuation of U.S. patent application Ser. No. 07/309,004 filed 7 Feb. 1989, now abandoned, which is a continuation of U.S. patent application Ser. No. 07/147,155, filed 22 Jan. 1988, now abandoned.

FIELD OF THE INVENTION

The present invention relates generally to systems for determining parameters of materials and, more particularly, but not by way of limitation to systems for nondestructive determining fiber volume fraction and resin porosity of composite materials constructed of at least two different constituent materials.

BRIEF DESCRIPTION OF THE INVENTION

The present invention provides a method for nondestructively determining fiber volume fraction and resin porosity of a composite material constructed of at least two different constituent materials wherein the following parameters of the composite material to be tested are known: density, elastic moduli of the constituent materials and layup sequence, the method comprising the steps of: propagating two acoustic waves of different polarizations through the composite material; receiving the acoustic waves propagated through the composite material; determining the velocity of each of the two acoustic waves propagated through the composite material from the received acoustic waves propagated through the composite material, the respective velocities being $V_1$ and $V_2$; determining the thickness of the composite material; and determining the fiber volume fraction and resin porosity of the composite material using the velocities, $V_1$ and $V_2$, the thickness and the known parameters of density, elastic moduli of the constituent materials and layup sequence. The present invention also provides an apparatus for nondestructively determining fiber volume fraction and resin porosity of a composite material constructed of at least two different constituent materials wherein the following parameters of the composite material to be tested are known: density, elastic moduli of the constituent materials and layup sequence, the apparatus comprising: means for propagating two acoustic waves of different polarizations through the composite material; means for receiving the acoustic waves propagated through the composite material and outputting the received acoustic waves in a digital format; means for determining the thickness of the composite material; and a processor receiving the two acoustic waves in a digital format and determining the velocity of each acoustic wave, $V_1$ and $V_2$, the processor having inputted therein the thickness of the composite material and having inputted therein the known parameters of density, elastic moduli of the constituent materials and layup sequence, the processor determining the fiber volume fraction and resin porosity of the composite material using the velocities, $V_1$ and $V_2$, the thickness and the known parameters of density, elastic moduli of the constituent materials and layup sequence.

In another aspect, the present invention provides an apparatus for nondestructively determining fiber volume fraction and resin porosity of a composite material constructed of at least two different constituent materials wherein the following parameters of the composite material to be tested are known: thickness, density, elastic moduli of the constituent materials and layup sequence, the apparatus comprising: means for propagating two acoustic waves of different polarizations through the composite material; means for receiving the acoustic waves propagated through the composite material and outputting the received acoustic waves in a digital format; means for determining the velocity of each of the two acoustic waves propagated through the composite material from the received and sensed acoustic waves propagated through the composite material and, the respective velocities being $V_1$ and $V_2$; and a processor receiving the two acoustic waves in a digital format and determining the velocities, $V_1$ and $V_2$, of the respective acoustic waves propagated through the composite material, the processor having inputted therein the known parameters of thickness, density, elastic moduli of the constituent materials and layup sequence, the processor determining the fiber volume fraction and resin porosity of the composite material using the velocities, $V_1$ and $V_2$, and the known parameters of thickness, density, elastic moduli of the constituent materials and layup sequence.

DESCRIPTION OF THE PREFERRED EMBODIMENTS

Figure 1:
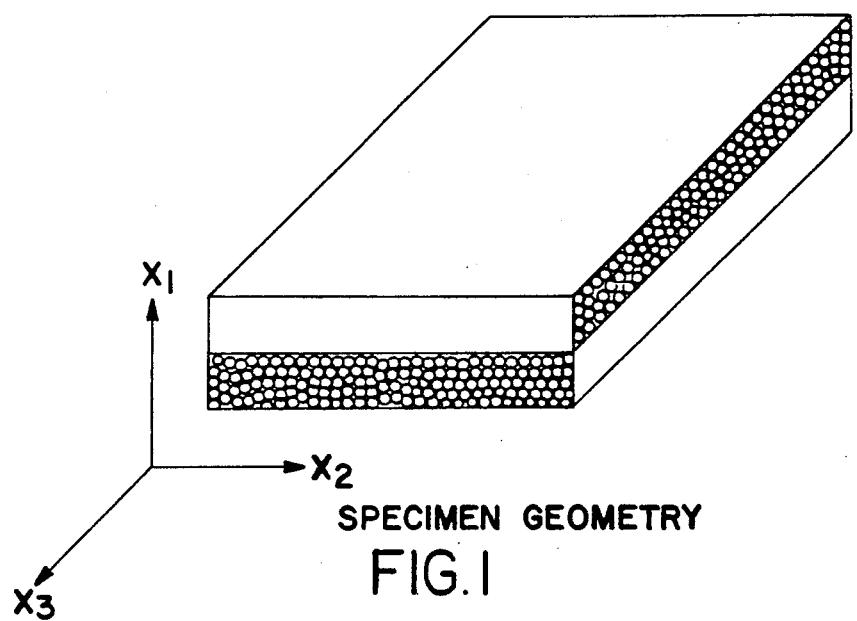
FIG. 1 is a diagrammatic view illustrating the geometry of a specimen of composite material to be tested.

In recent years the use of composite materials has increased significantly. In such materials, two different constituent materials are combined to optimize the properties of the resulting composite material. For example, high strength fibers are embedded in plastic materials to achieve a composite material which is light weight and has a high strength or stiffness to weight ratio. As used herein the term "composite materials" means any material constructed of at least two different constituent materials.

Inhomogeneities can develop during the processing stage when the laminate (composite material) is cured to its final solid state. Unwanted gases may be introduced into the composite material from a variety of sources including entrainment during mixing, entrapment of air between plies during layup and evolution of volatiles during the curing reaction. In an attempt to keep porosity at a minimum, a porous bleed ply usually is placed in contact with the laminate (composite material). In the fabrication process, temperature is increased: initially to lower the resin viscosity for better void and resin transport and ultimately to promote the cure reaction. Simultaneously, pressure is applied to force the unwanted gases and excess resin from the composite into the bleed ply, which is discarded after fabrication. During the process, fibers also can shift position, resulting in areas which are relatively resin rich or resin poor. When the process works properly, the result is a void-free microstructure with a uniform distribution of reinforcing fibers. When the process breaks down, weak areas with excess resin or porosity may be created.

The present invention provides a system for nondestructively determining fiber volume fraction, the percent of volume occupied by one of the constituent materials (fibers), and resin porosity, the percent of volume that is void or occupied by air, in composite materials.

In the present system, the following parameters of the composite material to be tested are taken as known: density, elastic moduli of the constituent materials and layup sequence.

Wave Propagation

The equations of motion for a continuum are given by:

$$\rho \ddot{u}_i = \sigma_{ij,j} \tag{1}$$

where
$\rho$ = density
$\underline{u}$ = particle displacement
$\sigma_{ij}$ = stress tensor components
and i signifies differentiation w.r.t. indicated subscript. By inserting the stress-strain relationship for an anisotropic solid:

$$\sigma_{ij} = C_{ijkl}\epsilon_{kl} \tag{2}$$

where
$C_{ijkl}$ = elasticity tensor components
$\epsilon_{kl}$ = strain tensor components
into the equations of motion, Eq. (1) becomes:

$$\rho \ddot{u}_i = C_{ijkl} u_{k,lj} \tag{3}$$

Assuming a plane wave solution of the form $$u_i = A_\sigma \alpha_i e^{j(k\underline{l}\cdot\underline{x} - wt)} \tag{4}$$

where
w = frequency
k = wave number
l = wave normal
$A_\sigma$ = amplitude of particle displacements
$\alpha$ = displacement (direction cosines)
we obtain the following eigenvalue equation for the velocities of ultrasonic wave propagation in any direction ($l_1$, $l_2$, $l_3$) in an anisotropic material $$\rho w^2 \alpha_i = C_{ijkl} k^2 l_j l_l \alpha_k \tag{5}$$

$$0 = (C_{ijkl} l_j l_l - \rho V_{ik}^2) \alpha_k, \quad V = \frac{w}{k}$$

The geometry of the problem is illustrated in FIG. 1, where the plane of fiber reinforcement has been chosen to be the $x_2 - x_3$ plane. Since most composite applications are for plate type structures, we are limited for most practical cases to wave propagation in the direction perpendicular to the reinforcing plane, i.e., $l = (1,0,0)$. For this case, the eigenvalue equation for an orthotropic material assumes the form:

$$\begin{pmatrix} C_{1111} - \rho V^2 & 0 & 0 \\ 0 & C_{1313} - \rho V^2 & 0 \\ 0 & 0 & C_{1212} - \rho V^2 \end{pmatrix} \begin{pmatrix} \alpha_1 \\ \alpha_2 \\ \alpha_3 \end{pmatrix} = \begin{pmatrix} 0 \\ 0 \\ 0 \end{pmatrix} \tag{6}$$

which yields three possible wave motions: one pure mode longitudinal wave with velocity $\sqrt{C_{1111}/\rho}$ and two pure mode shear waves with velocities $\sqrt{C_{1313}/\rho}$ and $\sqrt{C_{1212}/\rho}$. For wave propagation in any anisotropic material, one must be concerned with possible complications from energy flux deviations from the wave normal. However, for pure mode longitudinal wave propagation, energy can never deviate from the wave normal. Furthermore energy flux deviation is not observed for pure mode shear wave propagation in a direction perpendicular to a plane of reflection symmetry. Therefore, if we restrict our attention to symmetric laminates (this encompasses virtually all practical laminate stacking sequences), energy flux deviation may be safely neglected.

Material Properties

In order to assess the effects of resin porosity and fiber loading on ultrasonic behavior, it is necessary to first consider the behavior of a single ply in the context of micromechanics. Since voids will reside completely in the matrix, we begin by using the expressions of Boucher, "On the Effective Moduli of Isotropic Two-Phase Elastic Composites". *J. Composite Materials*, Vol. 8, 1974, pp. 82-89, to modify the material properties of an ideal matrix to account for the presence of porosity.

The next step in the procedure is to determine the mechanical properties of each individual ply from the known properties of the reinforcing fibers and the calculated properties of the resin. This micromechanics problem has been the subject of extensive research using a variety of different approaches. Unfortunately, there are no exact solutions available for the problem of a random array of cylindrical reinforcing fibers embedded in an isotropic matrix. However, several investigators have developed suitable expressions (bounds) for the elastic moduli of fiber reinforced composites which can be used as approximations for this purpose. In this investigation, the expressions developed by Hashin, "On the Elastic Behavior of Fiber Reinforced Materials of Arbitrary Transverse Phase Geometry," *J. Mech. Phys. Solids*, Vol. 13, 1965, pp. 119-134, for the upper bounds on the pertinent moduli were used, based on their accuracy and ease of implementation on a minicomputer.

Once the ply properties have been determined, it is then necessary to combine the individual properties in an appropriate manner for the particular stacking sequence to obtain the overall laminate properties. This is done using the equations of classical laminate theory.

The procedure for determining porosity and fiber volume fraction is outlined below.

Ultrasonic Velocity Measurement

A variety of analog techniques are available for the precise determination of transit time for ultrasonic wave propagation, Truell, R., Elbaum, C., and Chick, B., *Ultrasonic Methods in Solid State Physics*, Academic Press, 1969. Any of these methods would be acceptable for this purpose. However, the advent of high speed digital data acquisition and processing techniques means that this process can be automated. In this application we employ a technique developed by Egle, D., "Using the Acoustoelastic Effect to Measure Stress in Plates", UCDL-52914, Lawrence Livermore Laboratory (1980) to achieve this end. This process requires initially that the ultrasonic signals be digitized. An autocorrelation algorithm is then employed to estimate the transit time through the material. This estimate is then refined, using a curve fitting technique to find the maximum in the autocorrelation function. This approach has been found to yield the necessary accuracy in transit time measurements (to within 1 nanosecond) for microstructure characterization.

Data Analysis

Figure 2:
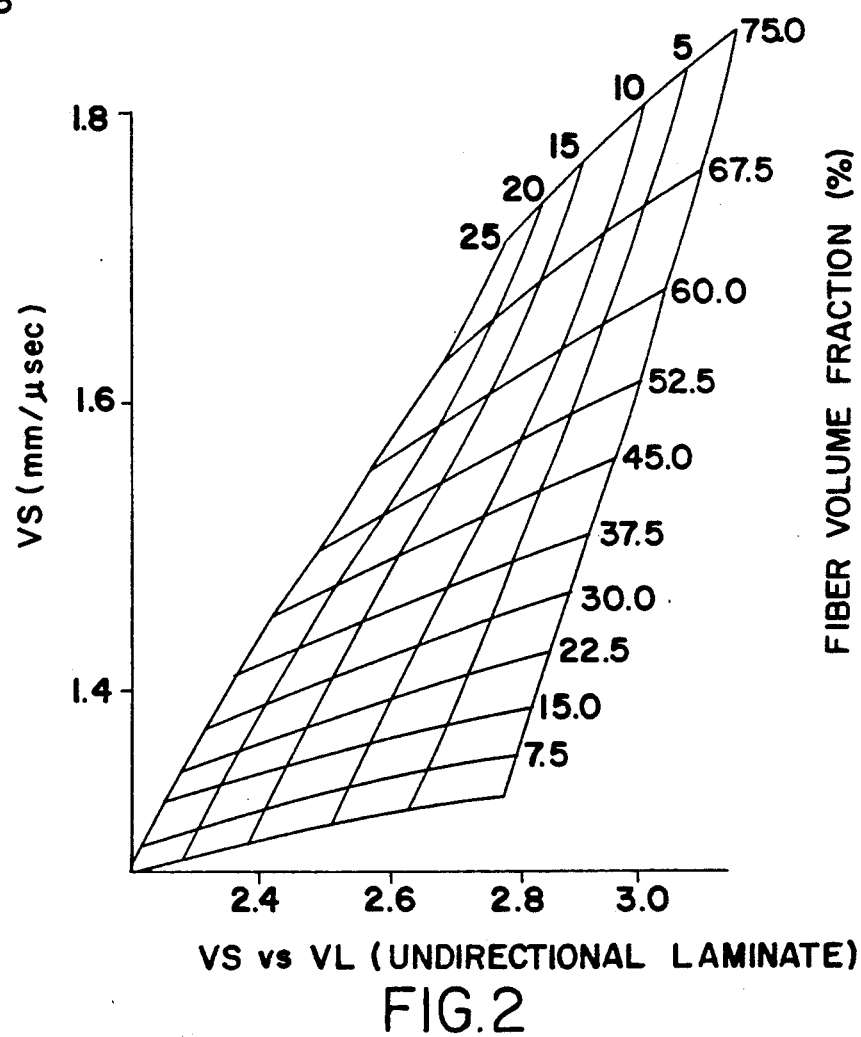
FIG. 2 is a chart illustrating the effects of fiber volume fraction and resin porosity on wave propagation for a typical graphite-epoxy laminate composite material.

The effects of fiber volume fraction and resin porosity on wave propagation for a typical graphite-epoxy laminate configuration are shown in FIG. 2. This figure is based on typical values for the mechanical properties of the constituent materials as shown in Table 1.

TABLE I

| Mechanical Properties of Composite Constituent Materials | | | | |
|---|---|---|---|---|
| | Density (gm/cc) | k (GN/m) | m (GN/m) | G (GN/m) |
| Resin | 1.26 | 7.7 | 2 | 2 |
| Graphite | 1.77 | 14.9 | 5.5 | 24 |

The layups studied in this program include a unidirectional laminate (shown) two cross-ply laminates, two angle ply laminates, and a quasiisotropic laminate. It should be noted that the velocity approach to fiber fraction/porosity measurement is also applicable to other composite systems (fiberglass, Kevlar, metalmatrix, etc.). However, resolution capability may vary from system to system, depending upon the relative differences in material properties between the fiber and matrix.

The algebraic complexity of the problem (see theoretical section) makes it relatively difficult to solve explicitly for even the simple case of unidirectional reinforcement. For practical laminates, the situation is even more complicated. Clearly, an alternative approach is needed. Ideally, this approach should be rapid, accurate, sufficiently flexible to handle various composite systems and configurations, reliable and easy implement on a commonly available device such as a personal computer. A computer code with these desired characteristics was developed.

Figure 3A:
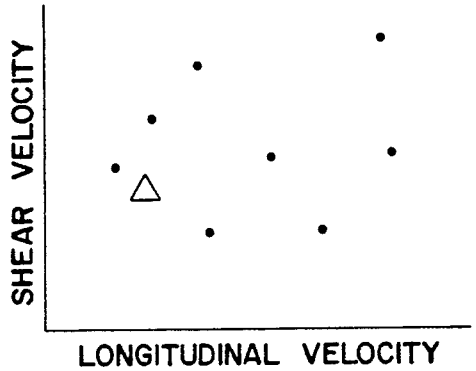
FIG. 3A, 3B and 3C are a series of three diagrams illustrating an iterative search algorithm for determining fiber volume fraction and resin porosity.
Figure 3B:
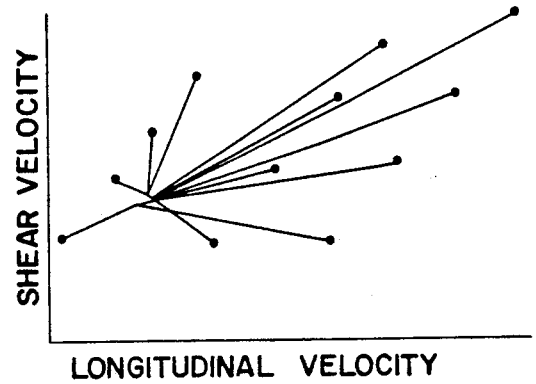
Figure 3C:
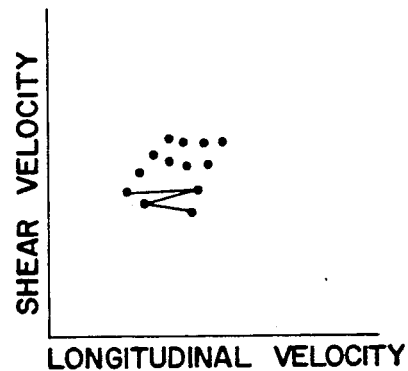

An iterative search algorithm was devised. It is illustrated in FIG. 3. First the points corresponding to the measured velocities are located for varying fiber volume fractions from 25% to 75% in 5% increments for the coarse mesh and resin porosities 0% to 25% in 5% increments. The distance in velocity space is given by:

$$\text{Distance} = [(VL_{Measured} - VL_{Calculated})^2 + (VS_{Measured} - VS_{Calculated})^2]^{\frac{1}{2}}$$

between each of the mesh points of the coarse mesh and the point corresponding to the measured velocities. The mesh point closest to the measured point is then the one which minimizes the distance measure as defined above. Once this point is identified, it serves as the base point for a new mesh with finer increments (+1% in both porosity and fiber content) than that of the original coarse mesh. The process is then repeated to identify the nearest point among the elements of the second mesh to that measured. Then, the entire process is repeated one last time with a relatively fine mesh (+0.1% increments) to establish the final solution. While further refinements are possible by repeating the process indefinitely, differences on this order have little physical significance and do not justify the additional time which would be required to further refine the calculation. The ability of the technique to resolve fine microstructural differences is also limited by the time resolution capability of the pulseecho overlap technique. In this case, we were capable of measuring transit time differences of 1 nanosecond.

Experimental Verification

In order to assess the utility of this technique, ultrasonic test results were compared with microscopic measurements of porosity and fiber volume fraction. Test samples were machined from a 24 ply, 30.5 cm ×30.5 cm unidirectionally reinforced panel manufactured by Lear Fan. This material was fabricated from Fiberite hy-E 1048 prepreg tape using standard autoclave processing techniques.

Figure 4:
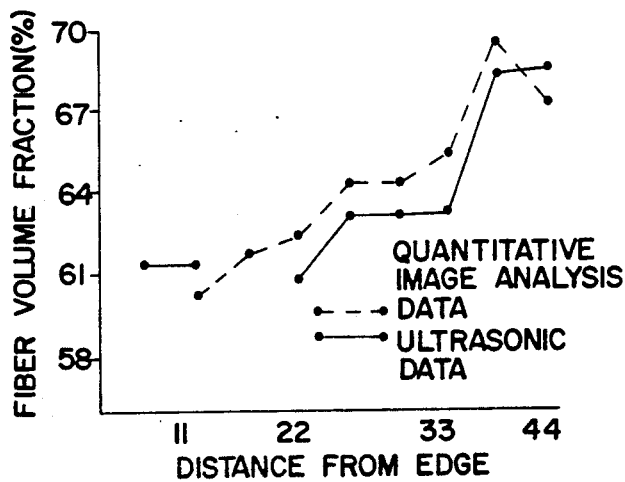
FIG. 4 is a comparison of ultrasonic and quantitative image analysis data.

Quantitative measurements of local fiber content and porosity and fiber volume fraction were made along the edges of selected samples using the ultrasonic technique described previously. These measured samples were sectioned and mounted in epoxy for microscopic analysis. Specimens were abrasively polished and placed in a microscope with quantitative image analysis capability (Quantamet) for automated measurement of microstructural constituents. Results from a typical sample are presented in FIG. 4. Good agreement, both qualitatively and quantitatively, was observed between the ultrasonic predictions of local fiber content and the microscopic measurements. Estimates of fiber loading from the two techniques were usually within 3% of each other. Both techniques predicted that there was negligible porosity present in the samples (less than 1.5%). Since there is an inherent uncertainty of 2% in the quantitative image analysis system, better agreement between the two methods was not expected. It should also be pointed out that the two techniques are not measuring precisely the same quantity. The ultrasonic test is sensitive to material property variations in a cylindrical volume (whose diameter is that of the transducer of 0.31 cm in this case). The image analysis approach measures changes averaged over a plane area (0.49 xm ×0.34 cm) rather than a volume. Given the level of material inhomogeneity observed in the velocity scans, some differences in the measurement techniques are to be expected.

Accordingly, it may be concluded that the results from the two methods are in substantive agreement, at least within experimental error.

Conclusions

1. A novel method for measuring local fiber content and porosity in composite materials has been developed.

2. The method is based upon a composite micromechanics model for the effects of fiber content and resin porosity on mechanical properties. The computer code developed in this research effort requires only ultrasonic velocity measurements for the microstructure determination.

3. The method is rapid, nondestructive, and applicable to virtually any composite material system with any stacking sequence.

4. Tests have been conducted on samples of a unidirectionally reinforced, 24 ply graphite-epoxy laminate to examine the utility of this method. Comparison of the predictions of local fiber content and porosity from the ultrasonic data and quantitative image analysis indicated that the two techniques were in substantial agreement with one another with the differences observed attributable to experimental error.

Figure 5:
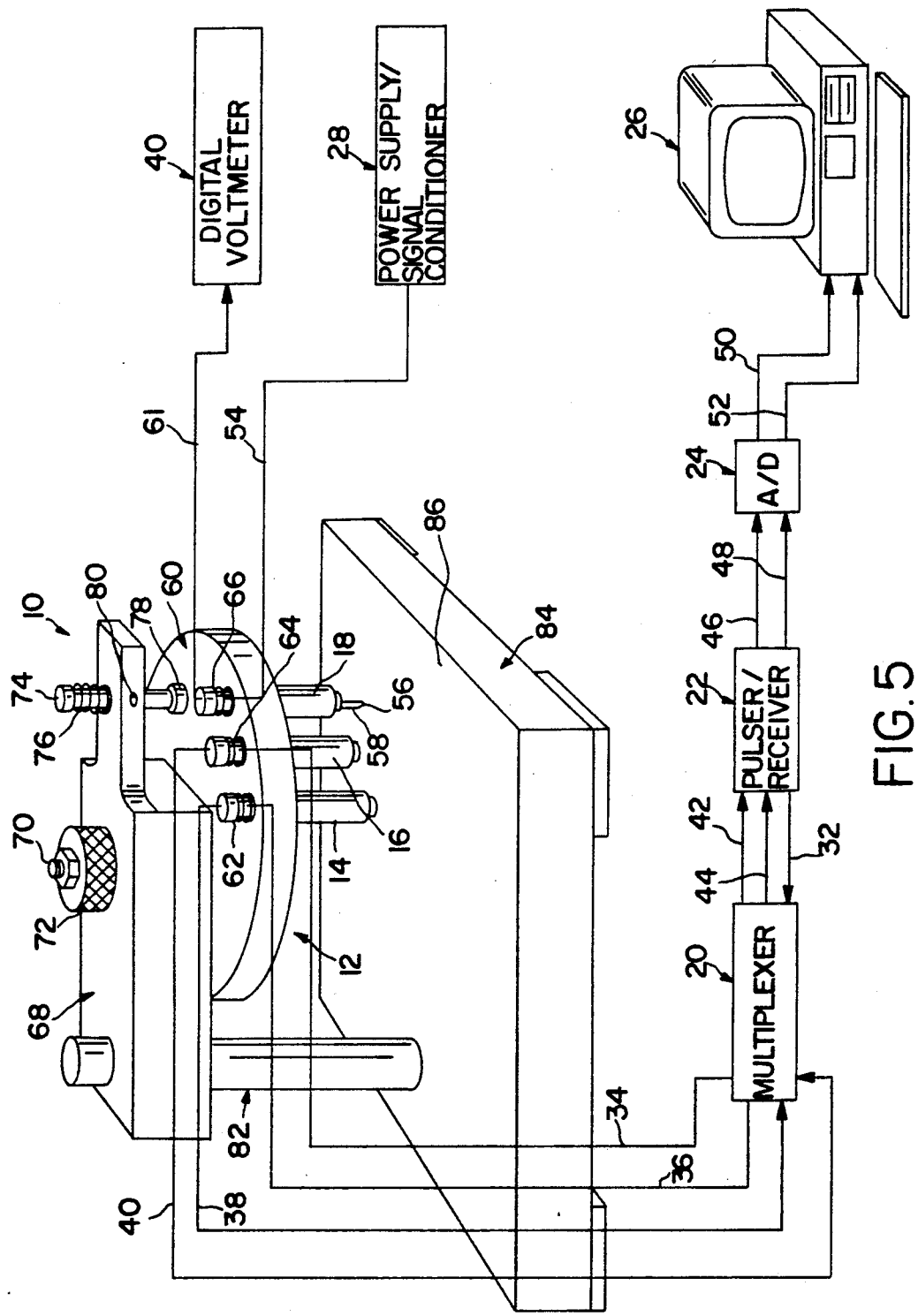
FIG. 5 is a diagrammatic, schematic view of a system constructed in accordance with the present invention for nondestructively determining fiber volume fraction and resin porosity of composite materials.

Embodiment of FIG. 5

Shown in FIG. 5 is a system 10 which is constructed to nondestructively determine fiber volume fraction and resin porosity of a composite material in accordance with the present invention and in accordance with the technique described in detail before. The system 10 basically includes: a support structure 12 for operatively supporting a shear transducer 14, a longitudinal transducer 16 and a linearly variable displacement transducer 18; a multiplexer 20; a pulser-receiver 22; an analog to digital converter 24 (designated A/D in FIG. 5); a processor 26; a power supply and signal conditioner 28; and a digital voltmeter 30. In one operational embodiment, the system 10 was constructed utilizing the following commercially available components:

| | |
|---|---|
| a. shear transducer 14 | Panametrics, Model V-155 |
| b. longitudinal transducer 16 | Panametrics, Model V-109 |
| c. linearly variable displacement transducer 18 | Shaevitz, Model PCA-220-005 |
| d. multiplexer 20 | Sonotek, Inc., Model 23HV |
| e. pulser-transducer 22 | Panametrics, Model 5052 |
| f. analog to digital converter 24 | Sonotek, Inc., Model STR *825 an associated software |
| g. processor 26 | Zenith, Model 248 |
| h. power supply and signal conditioner 28 | Albia Electronics Model DM-6 |
| i. digital voltmeter 30 | Hewlett Packard Model 3440 |

In the operational embodiment just described, the particular analog to digital converter 24, Sonotek, Inc. STR *825, plugs directly into the processor 26 and the software associated with this particular analog to digital converter 24 is operatively disposed in the processor 26 for operating the analog to digital converter 24.

The pulser receiver 22 is constructed and adapted to output timed excitation pulses over a signal path 32 to either the longitudinal transducer 16 or shear transducer 14. The pulser receiver also serves to amplify the sensed acoustic waves by the two transducers. The multiplexer 20 allows the operator to automatically switch between the longitudinal transducer 16 or shear transducer 14 as needed.

The excitation pulses are received by the shear transducer 14 or longitudinal transducer 16 and the transducers are constructed to cause an ultrasonic wave to propagate in the test sample, in response to receiving such excitation pulses.

The shear transducer 14 and the longitudinal transducer 16 each also are constructed to receive ultrasonic or acoustic waves propagated through the composite material being tested and to output in an analog format such received waves. The shear transducer 14 outputs received waves propagated through the composite material to be tested over a signal path 38. The longitudinal transducer 18 outputs in an analog format received waves propagated through the composite material to be tested over a signal path 40.

The waves propagated through the composite material are sensed by transducers and outputted by the shear transducer 14 and the longitudinal transducer 16 over the respective signal paths 38 and 40. These analog signals are inputted into and received by the multiplexer 20. The multiplexer 20 outputs the waves propagated through the composite material and received from the shear transducer 14 over a signal path 42 which are inputted into the pulser receiver 22. The multiplexer 20 also outputs the waves propagated through the composite material and received from the longitudinal transducer 16 over a signal path 44 which are inputted into the pulser receiver 22. The pulser receiver 22 outputs the waves propagated through the composite material in an analog format received from the shear transducer 14 over a signal path 46 which is inputted into the analog to digital converter 24. The pulser receiver 22 also outputs the waves propagated through the composite material in an analog format over a common signal path 48 which is inputted into the analog to digital converter 24.

The analog to digital converter 24 digitizes the received waves outputted by the shear transducer 14 and the analog to digital converter 24 outputs the digitized waves over a signal path 50. The analog to digital converter digitizes the waves outputted by the longitudinal transducer 16 and outputs the waves in a digital format over a signal path 52. The digitized waves outputted by the shear transducer 14 and the longitudinal transducer 16 respectively are inputted into the processor 26 by way of the respective signal paths 50 and 52.

The linearly variable displacement transducer 18 is connected to and receives power from the power supply and signal conditioner 28 over a signal path 54. The linearly variable displacement transducer 18 has a contact end 56 on a plunger 58 which is spring loaded and mounted within the casing of the linearly variable displacement transducer 18. The linearly variable displacement transducer 18 is constructed to output a dc voltage proportional to the displacement of the plunger 58 over a signal path 61 which is inputted into the digital voltmeter 40. The digital voltmeter 40 is constructed and adapted to provide a visually perceivable output indication of the voltage of the signal on the signal path 61 which is proportional to the displacement of the plunger 58 in the linearly variable displacement transducer 18 or, in other words, which is proportional to the thickness of the composite material as will be made more apparent below.

The shear transducer 14, the longitudinal transducer 16 and the linearly variable displacement transducer 18 are operatively mounted on the support structure 12. More particularly, the shear transducer 14 is disposed through an opening in a cylindrically shaped support plate 61 and the upper end of the shear transducer 14 is supported a distance above the upper surface of the support plate 60 by way of a spring 62 which is disposed about the shear transducer 14 and biases the shear transducer 14 in an upward direction. The longitudinal transducer 16 is disposed through an opening in the support plate 60 and the upper end of the longitudinal transducer 16 is support distance above the surface of the support plate 60 by way of a spring 64 which biases the longitudinal transducer 16 in an upwardly direction. The linearly variable displacement transducer 18 is disposed through an opening in the support plate 60 and the upper end of the linearly variable displacement transducer is supported a distance above the upper surface of the support plate 60 by way of a spring 66 which is disposed about the linearly variable displacement transducer 18.

The support plate 60 is disposed generally below an arm 68. A shaft 70 is disposed through a portion of the arm 68. One end of the shaft 70 is secured to a central portion of the support plate 60. The opposite end of the shaft 70 extends through a knob 72 and the shaft 70 is secured to the knob 72. The shaft 70 is connected to the support plate 60 and the knob 72 so that, by manually rotating the knob 72, the support plate 60 is rotated.

An actuator post 74 is disposed through an opening in one end of the arm 68 and the actuator post 74 is supported within this opening by way of a spring 76 so that one end of the actuator post 74 is supported a distance above the upper surface of the arm 68 by way of the spring 76. The actuator post 74 is supported on the arm 68 so that an actuating end 78 of the actuator post 74 is supported and disposed a distance above the upper surface of the support plate 60 in a nonactuated position of the actuator post 74. A set screw 80 is disposed through a portion of the arm 68 and one end of the set screw 80 is positioned to contact a portion of the actuator post 74 in one position of the set screw 80 to secure the actuator post 74 or the transducers 14 or 16 in a predetermined position within the respective openings in the arm 68 during the operation of the system 10 in a manner and for reasons which will be made more apparent below.

One end of the arm 68 is secured to one end of a support rod 82 and the opposite end of the support rod 82 is secured to a base 84. The support rod 82 cooperates to support the arm 68 and the support plate 60 a distance above an upper surface 86 of the base 84. The support rod 82 also is sized so that the shear transducer 14, the longitudinal transducer 16 and the linearly variable displacement transducer 18 each are supported a predetermined distance above the upper surface 86 of the base 84.

In operation, the composite material to be tested is placed on the upper surface 86 of the base 84 in a position generally under the plunger 58 contact end 56 of the linearly variable displacement transducer 18. The actuator post 74 is then pressed manually against the bias action of the spring 76 thereby moving the actuating end 78 into engagement with the upper end of the linearly variable displacement transducer 18. The actuator pulse 70 is manually moved in the downward direction until the upper end of the linearly variable displacement transducer 18 engages the upper surface of the support plate 60. The actuator post 74 can be secured in this position by the set screw 80 if desired. In this position of the linearly variable displacement transducer 18, the DC voltage outputted by the linearly variable displacement transducer 18 over the signal path 61 is proportional to the thickness of the composite material being tested and this voltage proportional to thickness is outputted over the signal path 61 and inputted into the digital voltmeter 40. The digital voltmeter 40 provides a visually perceivable output indication indicating the DC volt of the signal inputted on the signal path 61, this voltage being proportional to the thickness of the composite material. The operator manually inputs the thickness of the composite material into the processor 26 using the processor 26 keyboard.

It should be noted that, in a more automated form or if desired in a particularly application, the linearly variable displacement transducer 18 output signal proportional to the thickness of the material can be inputted directly into the processor 26 thereby eliminating the manually steps of reading the digital voltmeter 40 in manually inputting the thickness into the processor 26 if desired.

The actuator post 74 then is released and moved by the spring 76 to the rest position shown in FIG. 5 thereby causing the linearly variable displacement transducer 18 to be moved to the rest position by the spring 66. After the linearly variable displacement transducer 18 has been moved to the rest position, the operator then rotates the knob 72 thereby rotating the support plate 60 to position the upper end of the longitudinal transducer 16 generally under the actuating end 78 of the actuator post 74. The actuator post 74 then is moved downwardly against the bias action of the spring 76 with the actuating end 78 thereof engaging and moving the longitudinal transducer 16 in the downwardly direction. The longitudinal transducer 16 is moved in the downwardly direction by the actuator post 74 until the lower end of the longitudinal transducer 16 engages the upper surface of the composite material. The actuator post 74 is secured in this position by the set screw 80 thereby securing the longitudinal transducer 16 in the operating position wherein the lower end of the longitudinal transducer 16 engages the upper surface of the composite material.

It should be noted that, prior to moving the longitudinal transducer 16 to the operating position just described, a high viscosity coupling agent is applied to the lower end of the longitudinal transducer 16 for coupling the ultrasonic vibrations of the longitudinal transducer 16 to the composite material to be tested. Also, the high viscosity coupling agent is applied to a portion of the upper surface of the composite material to be tested. One coupling agent suitable for this purpose is a resin made by Dow Chemical, Model V9.

After the longitudinal transducer 16 has been moved to the operating position, the pulser receiver 22 is actuated to output excitation pulses which are multiplexed through the multiplexer 20 and inputted into the longitudinal transducer 16 by way of the signal path 34. The longitudinal transducer 16 is constructed to vibrate in a particular manner so that longitudinal ultrasonic waves are coupled to and propagated through the composite material. The ultrasonic waves induced by the longitudinal transducer 16 and propagated through the composite material to be tested propagate through the composite material and are reflected back through the composite material (back surface reflections in the particular embodiment of the invention shown in FIG. 5). The ultrasonic waves propagated through the composite material and reflected back through the composite material are sensed and received by the longitudinal transducer 16, and the longitudinal transducer 16 outputs an analog signal on the signal path 40 in response to receiving the ultrasonic waves propagated through the composite material. These received signals are outputted on the signal path 40 in an analog format. The signals outputted by the longitudinal transducer 16 on the signal path 40 are indicative of a second velocity ($V_2$), the velocity of the ultrasonic wave propagated through the composite material emanating from the longitudinal transducer 16.

The transducers 14, 16 and 18 must be positioned in the same position during the operation of the system 10 so the thickness measurement is taken and the ultrasonic waves are propagated through substantially the same point on the composite material. Index marks could be inscribed on the upper surface of the support plate 60 for alignment with one edge of the arm 68 to visually align each of the transducers 14, 16 and 18. In the alternative, index holes can be formed in the upper surface of the support plate 60 and a ball can be located in an opening in the lower surface of the arm 68 with the ball being biased toward the arm 68 by way of a spring. Thus, when the support plate 60 is rotated, the ball falls into one of the index holes in the support plate 60 to indicate that the support plate 60 has been rotated to a correct position.

The signals outputted by the longitudinal transducer 16 are multiplexed through the multiplexer 20 and inputted into the pulser receiver 22 by way of the signal path 44. The pulser receiver outputs such signals on a signal path 46 for reception by the analog to digital converter 24. The analog to digital converter 24 receives the signals in the analog format outputted by the longitudinal transducer 16 and the analog to digital converter 24, operated by the processor 26 in accordance with the program mentioned before for operating the analog to digital converter 24, digitizes the analog signals outputted by the longitudinal transducer 16. The analog digital converter 24 outputs in a digital format the longitudinal transducer 16 output signals on the signal path 52 which are inputted into the processor 26. The processor 26 is programmed to determined the second velocity ($V_2$) in response to receiving the inputted transducer 16 output signals in the digital format from the analog to digital converter 24.

The actuator post 74 then is released and moved by the spring 76 to the rest position shown in FIG. 5 thereby causing the longitudinal transducer 16 to be moved to the rest position by the spring 64. After the longitudinal transducer 16 has been moved to the rest position, the operator then rotates the knob 72 thereby rotating the support plate 60 to position the upper end of the shear transducer 14 generally under the actuating end 78 of the actuator post 74. The actuator post 74 then is moved downwardly against the bias action of the spring 76 with the actuating end 78 thereof engaging and moving the shear transducer 14 in the downwardly direction. The shear transducer 14 is moved in the downwardly direction by the actuator post 74 until the lower end of the shear transducer 14 engages the upper surface of the composite material. The actuator post 74 is secured in this position by the set screw 80 thereby securing the shear transducer 14 in the operating position wherein the lower end of the shear transducer 14 engages the upper surface of the composite material.

It should be noted that, prior to moving the shear transducer 14 to the operating position just described, a high viscosity coupling agent is applied to the lower end of the shear transducer 14 for coupling the ultrasonic vibrations of the shear transducer 14 to the composite material. One coupling agent suitable for this purpose is a resin made by Dow Chemical, Model V9, as mentioned before.

After the shear transducer 14 has been moved to the operating position, the pulser receiver 22 is actuated to output excitation pulses which are multiplexed through the multiplexer 20 and inputted into the shear transducer 14 by way of the signal path 34. The shear transducer 14 is constructed to vibrate in a particular manner so that shear ultrasonic waves of a known polarization are coupled to and propagated through the composite material. The ultrasonic waves induced by the shear transducer 14 and propagated through the composite material to be tested propagate through the composite material and are reflected back through the composite material (back surface reflection in the particular embodiment of the invention shown in FIG. 5). The ultrasonic waves propagated through the composite material and reflected back through the composite material are sensed and received by the shear transducer 14. The shear transducer 14 outputs an analog signal on the signal path 40 in response to receiving the ultrasonic waves propagated through the composite material, these received signals being outputted on the signal path 40 in an analog format. The signals outputted by the shear transducer 14 on the signal path 40 are indicative of the velocities of the two ultrasonic waves (($V_1$ and $V_2$) propagated through the composite material by the shear transducer 14.

The signals outputted by the shear transducer 14 are multiplexed through the multiplexer 20 and inputted into the pulser receiver 22 by way of the signal path 44. The pulser receiver outputs such signals on a signal path 46 for reception by the analog to digital converter 24. The analog to digital converter receives the signals in the analog format outputted by the shear transducer 14 and the analog to digital converter 24, operated by the processor 26 in accordance with the program mentioned before for operating the analog to digital converter 24, digitizes the analog signals outputted by the shear transducer 14. The analog to digital converter 24 outputs in a digital format the shear transducer 14 output signals on a signal path 52 which are inputted into the processor 26. The processor 26 is programmed to determined the first velocity ($V_1$) (the velocity of the factor of the two shear waves) in response to receiving the inputted transducer 16 output signals in a digital format from the analog to digital converter 24.

Prior to starting the operation of the system 10, the operator manually has inputted into the processor 26 certain parameters of the composite material to be tested, namely, density, elastic moduli of the constituent materials and layup sequence, which are stored in the processor 26. The processor 26 previously has the thickness of the composite material also has been inputted into the processor 26 in the manner described before. The processor 26 is programmed to store the inputted thickness of the composite material to be tested. After the processor 26 has determined the first and second velocities, $V_1$ and $V_2$, the processor 26 then is programmed to determined the fiber volume fraction and resin porosity of the composite material based on the determined parameters of thickness and first and second velocities, $V_1$ and $V_2$, and the inputted known parameters of density, elastic moduli of the constituent materials and layup sequence in accordance with the procedures graphically shown in FIGS. 2 and 3 and described before. In one particular embodiment, the processor 26 was programmed with the following program to enable the processor 26 to determine the fiber volume fraction and resin porosity of the composite material to be tested in the manner just described, the program being outlined below in the FORTRAN and C (subroutine PLT_Time) languages:

```
c      ------------------------------------------------
c      This program will compute the fiber volume
c      fraction and porosity of a laminated composite
c      (composed of layers of a uni-directional
c      composite material), based on the measured
c      longitudinal and shear velocities.
c      ------------------------------------------------
       interface to function pltime[c,alias:'_plot_
       time'] (n)
       integer n
       end
       interface to subroutine stinit[c]
       end
c
       dimension vl(11,11),vs(11,11),v1(11,11),v2(11,
11) space(3)
       dimension a(10,2)
       real c(2),t
       real mpsm, msm
       integer m1,m2,m3
       character infile*12
       common fsum,fden,rden,mpsm,msm,fpsm,ftsm,
flsm,nang
c
       data a,vl,vs,v1,v2/504*0.0/
       call stinit
       fsum = 0.0
c
c      ------INPUT MATERIAL PROPERTIES FOR----------
              ----------FIBER-MATRIX SYSTEM--------------
c
5      print*, ' ENTER THE NAME OF THE INPUT DATA
FILE'
       read(*,103) infile
103    format(a)
       open(3,file=infile,status='old')
       read(3,*) fden
       read(3,*) rden
       read(3,*) mpsm
       read(3,*) msm
       read(3,*) fpsm
       read(3,*) ftsm
       read(3,*) flsm
       rewind(unit=3)
       print*, ' ENTER THICKNESS OF THE SPECIMEN'
       read*, thick
       print*, ' ENTER NUMBER OF DIFFERENT ORIENTATION
ANGLES IN',
     &                  ' LAYUP'
```

```
      read*, nang
      do 10 i=1,nang
      print*, ' ENTER ORIENTATION ANGLE IN RADIANS'
      read*, a(i,1)
      print*, ' ENTER NUMBER OF PLIES AT THIS ANGLE'
      read*, a(i,2)
      fsum = fsum + a(i,2)
10    continue
c
c-------CALCULATE WAVE VELOCITY DATA---------
c
15    do 20 i = 2,1,-1
      t=pltime(n)
      e(i) = thick/(t*1000.)
20    continue
c
c-----------------SET AND REFINE MESH-------------
c
      space(1)=0.05
      space(2)=0.01
      space(3)=0.001
      ff=0.25
      fv=0.0
      do 25 k = 1,3
      call mesh(a,space(k),ff,fv,vl,vs,v1,v2)
      fmin = 1.e05
      do 30 i = 1,11
      do 40 j = 1,11
      fd = sqrt((vl(i,j) - c(1))**2 + (vs(i,j) -
c(2))/(2)
      if( fd .lt. fmin ) then
      fmin = fd
      imin = i
      jmin = j
      endif
40    continue
30    continue
c
c-----------SET LOWER LIMITS FOR NEW MESH----------
c
      if( k .lt. 3 ) then
      ff = v1(imin,jmin) - 5.*space(k+1)
      fv = v2(imin,jmin) - 5.*space(k+1)
      if(( fv .lt. 0.0 ) fv = 0.0
      endif
25    continue
      ff = v1(imin,jmin)*100.
      fv = v2(imin,jmin)*100.
      write(*,105) c(1)*1000.
      write(*,106) c(2)*1000.
105   format(1x,'THE LONGITUDINAL WAVE SPEED
IS:',1x,f7.1,1x,'m/s')
106   format(1x,'THE SHEAR WAVE SPEED
IS:',1x,f7.1,1x.'m/s')
      write(*,100) ff
      write(*,101) fv
```

```
100   format(1x,'THE FIBER VOLUME FRACTION
IS:',1X,f6.2 .' %')
101   FORMAT(1x,'THE RESIN VOID CONTENT IS:'1x,f6.2,'
%,/)
      write(*,102)
102   format(1x,'&0-STOP, 1-CONTINUE TESTING SAMPLE,
 2-CHANGE MATERIAL'
     & ,1x,'CONSTANTS')
      read(*,*) m1
      if(m1 .eq. 1) go to 15
      if(m1 .eq. 2) go to 5
      stop
      end
c
      subroutine mesh(a,s,ff,fv,vl,vs,v1,v2)
      dimension a(10,2),vl(11,11),vs(11,11),
 vl(11,11),v2(11,11)
      do 10 i=1,11
      vf = fv
      do 20 j=1,11
      call coef(a,ff,vf,ft1,ft2)
      vl(i,j)=ft1
      vs(i,j)=ft2
      vl(i,j)=ff
      v2(i,j)=vf
      vf=vf+s
20    continue
      ff=ff+s
      continue
      return
      end
c
      subroutine coef(a,ff,vf,ft1,ft2)
      dimension a(10,2)
      real mpsm,msm
      common fsum,fden,rden,mpsm,msm,fpsm,ftsmflsm,
 ,nang
      fve = vf
c     fve = vf/(1. - ff)
      ft = 1. - fve
      fdm = ft*rden
      fgs = msm*(9.*mpsm + 8.*msm)/(6.*(mpsm +
 2.*msm))
      fkm = mpsm*(1. - fve/(1. - ft*mpsm/(1.3333*msm
 + mpsm));
      fmm = msm*(1. - fve/(1. - ft*msm/(msm + fgs)))
      fdc = fdm + ff*(fden - fdm)
      fmc = (fkm + 2.*fmm)*(1. - ff)/(2.*fmm*(fkm +
 fmm))
      fmc = ff/(1./(ftsm - fmm) + fmc) + fmm
      fkc = fkm + ff/(1./(fpsm - fkm) + (1. -
 ff)/(fkm + fmm)) + fmc
      fgc = fmm + ff/(1./(flsm - fmm) + 1. -
 ff)/(2.1fmm)
      c44 = 0.0
      c66 = 0.0
```

```
      c46 = 0.0
      do 10 j = 1,nang
      ct = a(j,2)/fsum
      c44 = ct*(fmc*sin(a(j,1))**2 +
fgc*cos(a(j,1)))** 2) + c44
      c66 = ct*(fmc*cos(a(j,1))**2 +
fgc*sin(a(j,1))** 2) + c66sin(a(j,1))*
      c46 = ct*(cos(a(j,1))*sin(a(j,1))*(fgc - fmc))
 + c46
10    continue
      x = sqrt((c44+c66)**2 - 4.*(c44*c66 - c46**2))
      x1 = (c44 + c66 - x)/2.
      x2 = (c44 + c66 -x)/2.
      ft1 = sqrt(fkc/fdc)
      ft2 = sqrt(max(x1,x2)/fdc)
      return
      end
#include <stdlib.h>
#include <stdio.h>
#include <str_plx.h>
#include <str_str.h>
include <graph.h> struct plot sp[1]={1,1,608,15, 136,
73,198,2,0,1,2,1};

extern struct str sa[1];
    char buff[4096]={0};

int ipm = 2;
    int i,on[2]={1,0};
    unsigned int ick;
    int brd=0;
    int nbs=1;
    int ichar;
    int step=1;
    int     iret=0x0d,exc=0x1b,mov1=0x4b00,movr=
0x4d00,iend=0x1f00,movup=0x4800;
    int     pageup=0x4900,movdn=0x5000,pagedn=0x
5100,del=0x5300,ins=0x5200;
    int     start=70,mid=120,stop=160;

float plot_time(q)
    int q;
    {
    int width,mark[3];
    int ii,rmax,ro;
    int co[1024];
    int kmax,max;
    int j;
    float time;
    float f;

mode(14);
    vigen(11);
    attrib(&sp[0];
    grid(15,32,19,72,16,10,1,6);
```

```
    chrplt("Adjust Pulser-Receiver For Best
Waveform",170,18,15);
    chrplt("Hit ESC To Continue",240,38,18);
        /*data collection and plotting loop*/ sa[0].isr=7;
    i=sa[0].pdel[0]=0;
    sa[0].navg=6;
    j=1;
    chrplt("^",start,127,3);
    chrplt("^",mid,127,4);
    chrplt("^",stop,127,5);
    chrplt("Scanning Window Width =",220,0,7);
    coor(start,220,3);
    coord(mid,320,4);
    coord(stop,420,5);
    while(1){
        strbuf(&sa[0],buff);
        fplot(&ipm,&sp[0],buff;
        ipm=1;
    if(kbhit() != 0){
        ichar = getkey();
        if(ichar == exc)
        break;
        }
    else if(ichar == 's' || ichar == 'S'){
        coord(start+i,220,3);
        coord(mid+i,320,4);
        coord(stop+i,420,5);
        for(;;){
        ichar=getkey();
        if(ichar == exc)break;
        else if(ichar == del){
            for);;){
                ichar=getkey();
                coord(start+i,220,3);
                if(ichar == movl  &&
start > 50+step){
                chrplt("^",start,
127,3; );
                chrplt("^",start-=step,
127,3);
                }
                else if(ichar == movr && start
<mid-step){
chrplt("^",start,127,3);
                chrplt("^",start+=step,
127,3);
                }
                else if( ichar == movup)step
+=2;
                else if( ichar == movdn){
                    step -= 2;
                    if(step <= 1) step=1;
                }
                else if( ichar == iret
|| ichar  == exc){
```

```
                    break;
                    break;
                }
                else continue;
            }
        }
        else if(ichar == iend){
            for(;;){
                ichar=getkey();
                coord(mid+i,320,4);
                if(ichar == movl && mid
> start+step){
                    chrplt("^",mid,
127,4);
                    chrplt("^",mid-
=step, 127,1);
                }
                else if(ichar == movr
 && mid < step-step){
                    chrplt("^"mid,
127,1);
                    chrplt("^",mid+
=step,127,4);
                }
                else if( ichar == movup
)step+=2;
                else if( ichar =  movdn
){
                    step -= 2;
                    if(step <= 1)
 step=1;
                }
                else if( ichar == iret
|| ichar == exc){
                    break;
                    break;
                }
            }
        }
        else if(ichar == pagedn) {
            for(;;){
                ichar=getkey();
                coord(stop+i,420,5);
                if(ichar == movl && stop > mid
+step){
                    chrplt("^",stop,127,5
);
                    chrplt("^"stop-=step,
127,1);
                }
                else if(ichar == movr && stop
 < 591-step){
                    chrplt("^",stop,127,5
);
                    chrplt("^",stop+=step
,127,5);
                    {
```

```
                else if( ichar == movup)step+=
2;
                else if( ichar == movdn) {
                        step -= 2;
                        if(step <= 1) step=1;
                        }
                else if( ichar == iret || icha
r == exc){
                                break;
                                break;
                                }
                        }
                }
        else if( ichar == exc ) break;
        }
}
}
mark[0] = (start+i)*8;
mark[1] = (mid+i)*8;
width = mark[1] - mark[0];
ipm=0;
fplot(&ipm,&sp[0],buff);
_setvideomode(_DEFAULTMODE);
sa[0].isr = 10;
sa[0].pdel[0]=0;
strbufr\(&sa[0],buff);
for(ii=0; ii <=4096-mark[0]; ii==
        buff[ii] = buff[ii+mark[0]];
for(ii=4097-mark[0]; ii<= 4096; ii++)
        buff[ii] = 0;
rmax = 0;
kmax = 0;
mark[2] = (stop+i)*8 - mark[0];
for(ii=mark[2]-width; ii,= (mark[2]); ii++){
        ro=autocor(width,ii);
        co[ii-mark[2]] = ro;
        if(rmax < ro){
                rmax = ro;
                max = ii - mark[2];
                kmax = ii;
                }
        }
        f = ((float)(co[max-1] - co[max+1]))/((float)
(co [max-1]-2*co[max]+co[max+1]));
time = ((float) kmax) + f;
time *= 5.e-09;
return(time);
} char word[6][4]={"","","","","",""};
char window[2][5]={"",""};

coord(j,k,color)
int j,k,color;
{
        sprintf(word[color-3],"%d",j);
        chrplt(word[color],k,10,color);
```

```
            chrplt(word[color-3],k,10,color);
            sprintf(word[color],"%s",word[color-
3]);
            sprintf(window[0],"%d",mid-start);
            chrplt(window[1],420,0,7);
            chrplt(window[0],420,0,7);
            sprintf(window[1],"%s",window[0]);
    }
autocor(i,j)
int i,j;
{
int k;
float r=0.0
for(k=0; k<=i; k++){
        r += buff[k]*buff[k+j];
}
return(r);
}

NOTE: This program calls several subroutines:
    STINIT - board initialization routine
    STRBUF - collects data from A - D
             converter
    STRDRV - board driver
to acquire data from the digitizer. These
routines are commercially available from
Sonotek. For displaying waveforms, several
routines from the "Fastplot" library (also
available from Sonotek) are employed.
```

The signals outputted by the longitudinal transducer 16 and the shear transducer 14 comprise a first series of pulses generally referred to in the art as the "main bang" followed after a time delay by another series of pulses referred to generally in the art as "first back surface reflections", followed after a time delay by another series of pulses commonly referred to in the art as "second back surface reflections". This sequence of a series of pulses followed by a time delay and then another series of pulses is repeated. The analog to digital converter 24 digitizes this signal. The processor 26 could then be programmed to determine the velocity $(V_1)$ or $(V_2)$ by determining the time delay between corresponding peaks of the first and the second back surface reflections. However, in accordance with the program described above and in accordance with one mode of operating the present invention, the processor 26 is programmed to determine this time delay and thus determine the first and the second velocities, $(V_1)$ and $(V_2)$, using a quadratic fit to find the maximum in the autocorrelation function to determine the peak in each of the first and the back surface reflections and the time delay between these two peaks then is utilized to determine the respective velocities, $(V_1)$ and $(V_2)$.

It also should be noted that the particular analog to digital converter 24 describe before digitizes at a rate of 25 MKz. This rate of digitizing does not provide the accuracy desired in most applications of the system 10. Thus, the program mentioned before in connection with the particular analog to digital converter 24 cooperates the analog to digital converter 24 to artificially induce a higher accuracy by shifting the point in the analog signal to be digitized eight times thereby providing an effective digitizing rate or sample rate of 200 MHz in this particular example.

Rather than using the autocorrelation function system for determining the peaks for the purpose of measuring the velocities, $(V_1)$ and $(V_2)$, the processor 26 could be programmed to simply measure or determine the time delay between the peaks of the digitized signal. This is not done in the particular embodiment described before because this has been found not to be as accurate as the method previously described because of dispersion and attenuation phenomena. However, if the analog to digital converter 24 could be operated at a higher sampling or digitizing rate, this peak to peak method could be utilized for higher data acquisition.

With the particular model shown in FIG. 5 and particularly with the specific embodiment shown described before, the outputs of the shear transducer 14 and the longitudinal transducer 16 are displayed by the processor 26 so the operator can determine whether or not the received signals are adequate for processing in accordance with the present invention. The operator is observing these signals on the processor 26 display to ascertain whether or not the amplitudes are high enough or, in other words, whether or not this is a detectable signal. The processor 26 in some applications could be programmed to make this determination automatically.

As specifically described before, the system 10 utilizes a shear transducer 14 and a longitudinal transducer 16. In the shear transducer 14, vibrations are generated in response to the received excitation pulses and these vibrations result in the first ultrasonic wave being emitted from the shear transducer 14 and propagated through the composite material to be tested. Assuming "$\underline{l}$" equals a vector describing the direction of propagation of the ultrasonic wave normal, and "$\underline{a}$" equals a vector describing the direction of particle vibration in the composite material, then the ultrasonic wave propagated through the composite material as a result of a shear transducer 14 represent a circumstance where "$\underline{l}$" is perpendicular to "$\underline{a}$".

As specifically described before, the system 10 also utilizes a longitudinal transducer 16. In the longitudinal transducer 16, vibrations are generated in response to the received excitation pulses and these vibrations result in the second ultrasonic wave being emitted from the longitudinal shear transducer 16 and propagated through the composite material to be tested in this circumstance, "$\underline{l}$" is parallel to "$\underline{a}$". Assuming "$\underline{l}$" equals a vector describing the direction of propagation of the ultrasonic wave normal, and "$\underline{a}$" equals a vector.

Thus, the waves propagated through the composite material as induced by the shear transducer 14 and the longitudinal transducer 16 have different polarizations, one instance, being were "$\underline{l}$" is parallel to "$\underline{a}$" in the case of the longitudinal transducer 16 and the other being were "$\underline{l}$" is perpendicular to "$\underline{a}$" in the case of the shear transducer 14. In the present invention, it only is important that two acoustic waves are propagated through the composite material to be tested having different polarizations and the present application is not limited to the particular polarizations described before with respect to the longitudinal and the shear transducers 16 and 14.

It also should be noted that two waves having different polarizations can be caused to be propagated through the composite material to be tested using only a single shear transducer. In this instance, the composite material to be tested is placed in one position under the single shear transducer for inducing the first ultrasonic wave to be propagated through the composite material. The composite material then is moved and repositioned under the shear transducer for propagating the second ultrasonic wave through the composite material. If the composite material is moved in a proper manner to different positions as just described, two waves having different polarizations can be induced in the composite material using the signal shear transducer.

The specific program described before is particularly adapted for composite materials wherein the fiber constituent is disposed in the other material constituent in a two dimensional pattern. The present invention also could be utilized for three dimensional patterns; however, the processor 26 program would have to be modified to accommodate such three dimensional patterns. In general, the program would have to be modified in the following manner to accommodate three dimensional patterns for woven reinforcements, or for carbon-carbon materials.

EMBODIMENT OF FIG. 6

Figure 6:
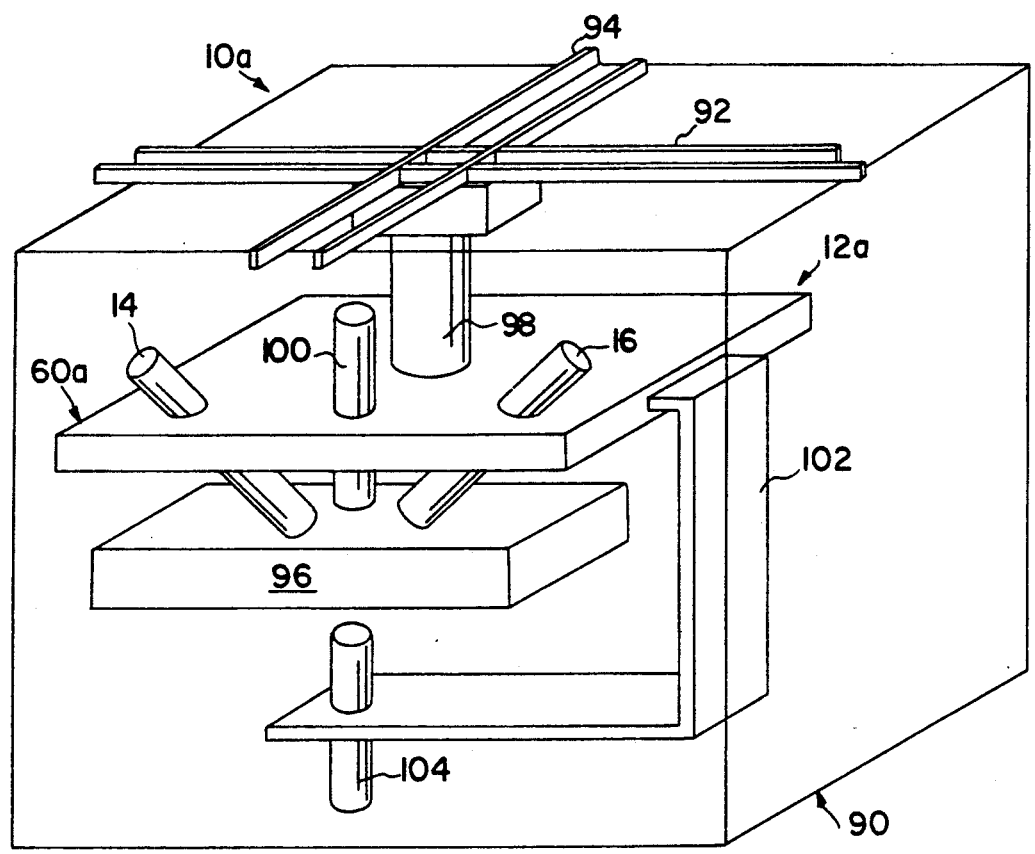
FIG. 6 is another system which is constructed in accordance with the present invention for nondestructively determining fiber volume fraction and resin porosity of composite materials.

Shown in FIG. 6 is a system 10a which also is constructed in accordance with the present invention for nondestructively determining fiber volume fraction and resin porosity of a composite materials. The system 10a generally comprises a modified support structure 12a which is disposed in a reservoir 90 containing water, the support structure 12a being immersed in the water.

The support structure 12a is connected to cross beams 92 and 94 which are supported on the upper end of the reservoir 90. In this embodiment, the composite material to be tested also is immersed within the reservoir as generally illustrated diagrammatically in FIG. 6 wherein the composite material is designated by the reference numeral 96.

The support structure 12a includes a modified support plate 60a which is rollingly connected to the cross beams 92 and 94 by way of a support beam 98, one end of the support beam 98 being secured to the support plate 60a and the opposite end of the support beam 98 being rollingly connected to the cross beams 92 and 94 so the support plate 60a can be moved along the support beam 92 and alternatively along the support beam 94 for positioning the support plate 92 in various positions within the reservoir 90 and with respect to the composite material 96.

In this embodiment, four longitudinal transducers are used. One pair (100 and 104) are employed at normal incidence for longitudinal wave propagation. A second pair (14 and 16) are employed at an incidence angle other than 90° and are used to generate shear waves via mode conversion. In this way, transducers 100 and 104 can be used for thickness measurement (since they are a known distance apart and the sound velocity in water is constant) as well as for longitudinal wave propagation.

One end of a curved arm 102 is connected to the support plate 60a. The arm 102 extends a distance from the support plate 60a so the opposite end of the arm 102 is positioned generally below and spaced a distance from the first thickness transducer 100. A second thickness transducer 104 is supported in the end of the arm 102, opposite the end connected to the support plate 60a, so that the second thickness transducer 104 is aligned with the first thickness transducer 100. The second thickness transducer 104 also is constructed and operates exactly like the longitudinal transducer 16 described before.

The transducers 14, 16, 100 and 104 each are connected through the multiplexer 20, the pulser receiver 22, the analog to digital converter 24 and the processor 26 in a manner exactly like that described before with respect to the transducers 14 and 16.

In operation, the composite material to be tested is disposed in the immersion bath within the reservoir 90. The support structure 12a is positioned on the cross beam 92 or the cross beam 94 so that transducer 100 is positioned generally above a point on the composite material 96 and transducer 104 is positioned generally on the opposite side of the composite material 96 and aligned with the first thickness transducer 100. In this position, the transducer 14 is angularly disposed within the support plate 60a so that the ultrasonic wave emitted by the transducer 14 impinges on the point immediately below the first thickness transducer 100 and generally between the first and the second thickness transducers 100 and 104. In this position, transducer 16 is angularly disposed within the support plate 60 so that the ultrasonic waves generated in the part by transducer 14 will be received by transducer 16.

Transducer 14 and transducer 16 are operated in a pitch-catch mode rather than the pulse-echo mode described in FIG. 5. Otherwise, they are used to provide shear velocity information analogous to that provided by the single contact shear transducer shown in FIG. 5 (14).

Transducer pair 100 and 104 are used for two purposes. The first purpose is to determine the thickness of the composite sample. For this purpose, transducer 100 is excited by the pulser receiver 22 to generate a longitudinal wave in the water. This wave propagates to the upper surface of the composite material where part of the energy is reflected back to transducer 100. The reflected wave and successive reflections are sensed by this transducer. Since the velocity of sound wave propagation in water is a known constant (1,460 m/s), by digitizing the response of transducer to the first two water path reflections, the distance between transducer 100 can be determined. In a similar fashion, by exciting transducer 104 and digitizing the same two water path echoes, its position relative to the lower surface of the composite is determined. Since the total distance between the surface of transducer 100 and transducer 104 is fixed, this procedure yields the thickness of the composite.

The second purpose of the transducer pair is to determine the velocity of longitudinal wave propagation in a direction perpendicular to the plane of reinforcement. The device may be operated in a pulse-echo mode with a single transducer (either 100 or 104) serving as generator and receiver or with one transducer serving as generator and the other as receiver. By now analyzing successive internal reflections within the composite, the transit time for this digital mode can be measured. This, in conjunction with the thickness measurement, yields the desired longitudinal velocity ($V_2$).

In this operation of system 10a, the first and second velocities are determined in a manner similar to that described with respect to system 10 and the processor is programmed to calculate resin porosity and fiber volume fraction as in system 10. The processor is also programmed to translate the transducer assembly over the surface of the part so that resin porosities and fiber volume fraction measurements can be performed for the entire part.

EMBODIMENT OF FIG. 7

Figure 7:
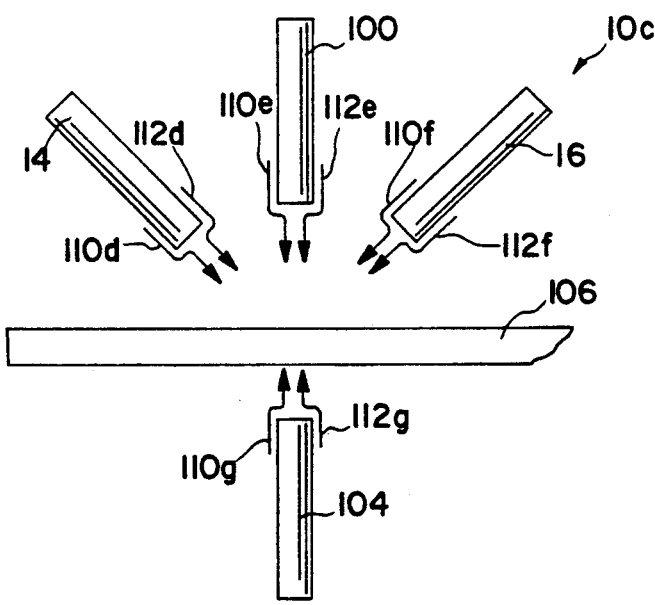
FIG. 7 is yet another system constructed in accordance with the present invention for nondestructively determining fiber volume fraction and resin porosity of composite materials.

Shown in FIG. 7 is another modified system 10c which is constructed in accordance with the present invention for nondestructively determining fiber volume fraction and resin porosity of a composite material, the composite material being diagrammatically shown in FIG. 7 and designated therein by the reference numeral 106. In this system 10c, the transducer 14 and the transducer 16 each are supported in a support plate (not shown) in a manner exactly like described before with respect to the system 10a shown in FIG. 6. Further, transducer 100 is supported in the support plate in a manner exactly like described before with respect to the system 10a shown in FIG. 6. Transducer 104 is supported so the second thickness transducer 104 is disposed and oriented with respect to the first thickness transducer 100 in a manner exactly like that described before with respect to the system 10a shown in FIG. 6.

In system 10c, a pair of water jets 112 are associated with each of the transducers 14, 16, 100 and 104. The water jets associated with the transducers 14, 16, 100 and 104 are schematically shown and represented in FIG. 7 by a pair of arrows associated with each transducer and designated by the reference numerals 110 and 112. The water jets associated with the transducer 14 are designated as 110d and 112d in FIG. 7, the water jets associated with the transducer 100 are designated 110e and 112e in FIG. 7, the water jets associated with the transducer 16 are designated 110f and 112f in FIG. 7 and the water jets associated with the transducer 104 are designated 110s and 112s in FIG. 7. The water jets 110 and 112 associate with each of the transducers are oriented to supply a jet of water generally between the end of the transducer and the surface of the composite material 106.

The water jets or streams provided by the water jets 110 and 112 provide a coupling for coupling the ultrasonic waves between the transducers and the composite material 10 thereby eliminating the need for immersing the transducers and the composite material in a reservoir containing the coupling agent as described before in connection with FIG. 6.

In this embodiment of the invention, the transducers 14, 16, 100 and 104 can be moved freely about the composite material 106. This embodiment of the invention permits the testing of large parts which are incapable of being immersed practically in a reservoir.

In this embodiment of the invention, the fiber volume fraction and resin porosity of the composite material are determined by the processor 26 in a manner exactly like that described before with respect to the system 10a shown in FIG. 6.

The procedures prescribed in detail before assume the state of cure of the composition material is known and therefore the elastic modulii of the constituent materials also are known. The elastic moduli of the constituent materials of the composite material vary with the state of cure and, where the state of cure is not known, procedures must be effected to measure the effect of the cure reaction in the composite material. Preferably, the procedures are compatible with ultrasonic sound measurements. In general, dielectric property measurements (conductivity, capacitance, permitivity, loss factor) can be used to accomplish this purpose.

Since ionic mobility is directly related to the extent of polymerization, measurement of conductivity can be correlated to the degree of cure. Hence, mechanical properties (Young's modulus, shear modulus, Poisson's ration, viscosity, etc.). It should be pointed out that these correlations are empirical and must be done for each resin system under consideration. See Marvin Bramm Berg, David Day, Huan Lee and Kimberly Russell "New Applications For Dielectric Monitoring and Control In Advanced Composites: The Latest Developments", Published by American Society of Metals (1986, pages 307–311). These relationships are the basis for the present method of compensating for local variations in the extent of cure. It should also be mentioned that low frequency probes must be used for accurate cure measurements.

Initially, what is sometimes referred to herein as a "state of cure data base" is accumulated. Sample composite materials, each having the same constituent material as the composite material to be tested and each having a known state of cure, initially are established. Each of these sample composite materials is cured to various known states of cure, such as ten percent (10%) cured, twenty percent (20%) cured . . . one hundred percent (100%) cured, for example. The elastic moduli (shear and Young's moduli for example) and the dielectric property (e.g. conductivity) of each of these resin samples then is determined.

From this set of experimental or empirical data, curves plotting two independent elastic moduli such as shear and Young's versus conductivity for each of the sample composite materials are developed. These curves comprise the state of cure data base which is inputted into the processor 26. In a more preferred form, a formula is developed representing each of these curves and these formulae comprise the state of cure data base which is inputted into the processor 26. In either case, the state of cure data base is inputted into and stored in the processor 26.

The dielectric property measuring device outputs a signal which is indicative of the conductivity of the composite material to be tested.

Dielectric property devices which are capable of providing an output proportional to the capacitance of the composite material to be tested are well known in the art and one such device which can be used in the present invention is commercially available from Micromet Instruments, Inc , Eumetric System II The dielectric constant indicating device outputs an indication of the dielectric constant of the composite material being tested, and this output is digitized and inputted into the processor 26. Where the dielectric constant indicating device more particularly outputs an indication of the conductivity of the composite material to be tested, the processor 26 is programmed to determine the dielectric constant of the material to be tested from the inputted indication of measured conductivity.

The processor 26 has stored therein the state of cure data base, and the processor 26 is programmed to determine the shear modulus and the Young's modulus from the inputted output of the dielectric constant indicating device either from the curves stored in the state of cure data base or the formula stored in the state of cure data base.

After determining the required elastic modulii, the processor 26 then determines the other composite material parameters in the manner described before, but using the shear modulus and the Young's modulus determined in the manner just described.

With respect to the device as shown in FIGS. 6 and 7, the dielectric constant indicating device cannot be incorporated with the other transducers since water is used as the transmitting medium In these cases, the dielectric constant indicating device which provides an output of the capacitance of the composite material being tested cannot be used in a water medium In these instances where water is used as a transmitting medium, the dielectric constant indicating device separately is utilized to determine the dielectric constant of the composite material being tested.

Further, with respect particularly to the embodiment shown in FIGS. 6 and 7, it should be noted that the state of cure may, and in many instances will, vary over the area of composite material being tested For example only, the state of cure along the edges of the composite material may be quite different as compared to the state of cure over the central portion of the composite material to be tested. The dielectric property of the composite material to be tested is determined at a plurality of points over the entire area of the composite material to be tested and the determined dielectric property are correlated with the other measured parameters for determining the parameters in accordance with the present invention.

Changes may be made in the construction and the operation of the various components and assemblies described herein and changes may be made in the steps or the sequence of steps of the methods described herein without departing from the spirit and the scope of the invention as defined in the following claims.

I claim:

1. A method, using a processor, for nondestructively determining fiber volume fraction and resin porosity of a composite material constructed of at least two different materials wherein the following parameters of the composite materials to be tested are known: density and layup sequence, the method comprising:

determining the elastic moduli of the composite material to be tested and inputting the elastic moduli into the processor;

propagating two independent acoustic waves through the composite material;

receiving the acoustic waves propagated through the composite material in the processor;

determining, in the processor, the velocity of each of the two acoustic waves, propagated through the composite material from the received acoustic waves propagated through the composite material, the respective velocities being $V_1$ and $V_2$;

determining the thickness of the composite material and inputting the thickness into the processor; and determining, in the processor, the fiber volume fraction and resin porosity of the composite material using the determined elastic moduli, the velocities, $V_1$ and $V_2$, the thickness, and the known parameters of density and layup sequence.

2. The method of claim 1 wherein the step of determining the elastic moduli is defined to further comprise:

determining the dielectric constant of the material to be tested; and determining the elastic moduli of the material to be tested from the determined dielectric constant; and inputting the elastic moduli into the processor.

3. The method of claim 2 wherein the step of determining the elastic moduli from the determined dielectric constant is further defined as comprising:

providing sample composite materials, each sample composite material having material constituents substantially the same as the composite material to be tested and each sample composite material having a different state of cure;

determining the shear modulus and the Young's modulus and the dielectric constant of each of the sample composite materials to provide a correlation between the Young's modulus and the dielectric constant and the correlation between the shear modulus and the dielectric constant of each of the sample materials which comprises a state of cure data base;

determining the dielectric constant of the composite material to be tested; and determining the elastic moduli comprising the shear modulus and the Young's modulus of the composite material to be tested using the measured dielectric constant of the composite material to be tested and the state of cure data base.

4. The method of claim 1 wherein the acoustic waves are defined further as being ultrasonic waves.

5. The method of claim 4 wherein the steps of propagating the two acoustic waves is defined further as propagating two acoustic waves through the composite material with one wave being a longitudinal wave and the other wave being a shear wave.

6. An apparatus for nondestructively determining fiber volume fraction and resin porosity of a composite material constructed of at least two different constituent materials wherein the following parameters of the composite materials to be tested are known: density and layup sequence, the apparatus comprising:
 means for determining the elastic moduli of the composite material to be tested;
 means for propagating two independent acoustic waves through the composite material;
 means for receiving the acoustic waves propagated through the composite material and outputting the received acoustic waves in a digital format;
 means for determining the thickness of the composite material; and
 a processor receiving the two acoustic waves in a digital format and determining the velocity of each of the acoustic waves, $V_1$ and $V_2$, the processor having inputted therein the thickness of the composite material and the processor having inputted therein the elastic moduli of the composite material to be tested and the processor having inputted therein the known parameters of density and layup sequence, the processor determining the fiber volume fraction and resin porosity of the composite material using the velocities, $V_1$ and $V_2$, the thickness, the elastic moduli and the known parameters of density and layup sequence.

7. An apparatus for nondestructively determining fiber volume fraction and resin porosity of a composite material constructed of at least two different constituent materials wherein the following parameters of the composite material to be tested are known: thickness, density and layup sequence, the apparatus comprising:
 means for determining the elastic moduli of the composite material to be tested;
 means for propagating two independent acoustic waves through the composite material;
 means for receiving the acoustic waves propagated through the composite material and outputting the received acoustic waves in a digital format;
 means for determining the velocity of each of the two acoustic waves propagated through the composite material from the received and sensed acoustic waves propagated through the composite material and, the respective velocities being $V_1$ and $V_2$; and
 a processor receiving the two acoustic waves in a digital format and determining the velocities, $V_1$ and $V_2$, of the respective acoustic waves propagated through the composite material, the processor having inputted therein the known parameters of thickness, density and layup sequence and the processor having inputted therein the determined elastic moduli, the processor determining the fiber volume fraction and the resin porosity of the composite material using in the velocities, $V_1$ and $V_2$, the determined elastic moduli and the known parameters of thickness, density and layup sequence.

8. A method, using a processor, for nondestructively determining fiber volume fraction and resin porosity of a composite material constructed of at least two different materials wherein the following parameters of the composite material to be tested are known: density and layup sequence, the method comprising:
 determining the elastic moduli of the composite material to be tested;
 propagating two independent acoustic waves from acoustic wave sources through the composite material at different positions over the surface area of the composite material to be tested;
 coupling the acoustic waves from the acoustic wave sources to the composite material with a fluid medium;
 receiving the acoustic waves propagated through the composite material;
 determining, in the processor, the velocity of each of the two acoustic waves propagated through the composite material from the received acoustic waves propagated through the composite material, the respective velocities being $V_1$ and $V_2$;
 determining the thickness of the composite material and putting the thickness into the processor; and
 determining, in the processor, the fiber volume fraction and resin porosity of the composite material using the determined elastic moduli, the velocities, $V_1$ and $V_2$, the thickness and the known parameters of density and layup sequence.

9. The method of claim 8 wherein the step of determining the elastic moduli is defined further to comprise:
 determining the dielectric property of the material to be tested; and
 determining the elastic moduli of the material to be tested from the determined dielectric property.

10. The method of claim 8 wherein the step of determining the elastic moduli from the determined dielectric property is further defined as comprising:
 providing sample composite materials, each sample composite material having material constituents substantially the same as the composite material to be tested and each sample composite material having a different state of cure;
 determining the elastic moduli (two independent moduli) and the dielectric property of each of the sample composite materials to provide a correlation between the two moduli and the dielectric property which comprises a state of cure data base;
 determining the dielectric property of the composite material to be tested; and
 determining the elastic moduli (two independent moduli) of the composite material to be tested using the measured dielectric property of the composite material to be tested and the state of cure data base.

11. The method of claim 8 wherein the acoustic waves are defined further as being ultrasonic waves.

12. The method of claim 11 wherein the steps of propagating the two acoustic waves is defined further as propagating two acoustic waves through the composite material with one wave being a longitudinal wave and the other wave being a shear wave.

13. An apparatus for nondestructively determining fiber volume fraction and resin porosity of a composite material constructed of at least two different constituent materials wherein the following parameters of the composite materials to be tested are known: density and layup sequence, the apparatus comprising:
 means for determining the elastic moduli of the composite material to be tested;
 means for propagating two independent acoustic waves through the composite material;
 means for providing a fluid medium for coupling the acoustic waves to the composite material;
 means for receiving the acoustic waves propagated through the composite material and outputting the received acoustic waves in a digital format;
 means for determining the thickness of the composite material; and
 a processor receiving the two acoustic waves in a digital format and determining the velocity of each of the acoustic waves, $V_1$ and $V_2$, the processor having inputted therein the thickness of the composite material and the processor having inputted therein the elastic moduli of the composite material to be tested and the processor having inputted therein the known parameters of density and layup sequence, the processor determining the fiber volume fraction and resin porosity of the composite material using the velocities, $V_1$ and $V_2$, the thickness, the elastic moduli and the known parameters of density and layup sequence.

14. An apparatus for nondestructively determining fiber volume fraction and resin porosity of a composite material constructed of at least two different constituent materials wherein the following parameters of the composite material to be tested are known: thickness, density and layup sequence, the apparatus comprising:

means for determining the elastic moduli of the composite material to be tested;

means for propagating two independent acoustic waves through the composite material;

means for providing a fluid medium for coupling the acoustic waves to the composite material;

means for receiving the acoustic waves propagated through the composite material and outputting the received acoustic waves in a digital format;

means for determining the velocity of the two acoustic waves propagated through the composite material, the respective velocities being $V_1$ and $V_2$; and a processor receiving the two acoustic waves in a digital format and determining the velocities, $V_1$ and $V_2$, of the respective acoustic waves propagated through the composite material, the processor having inputted therein the known parameters of thickness, density and layup sequence and the processor having inputted therein the determined elastic moduli, the processor determining the fiber volume fraction and the resin porosity of the composite material using in the velocities, $V_1$ and $V_2$, the determined elastic moduli and the known parameters of thickness, density and layup sequence.

* * * * *